United States Patent [19]

Walraevens et al.

[11] 4,000,204
[45] Dec. 28, 1976

[54] PROCESS FOR THE PURIFICATION OF VINYLIDENE CHLORIDE

[75] Inventors: René Walraevens; André Devos, both of Brussels, Belgium

[73] Assignee: Solvay & Cie, Brussels, Belgium

[22] Filed: July 29, 1975

[21] Appl. No.: 600,158

[30] Foreign Application Priority Data

Aug. 2, 1974 Belgium .............................. 147226

[52] U.S. Cl. ........................ 260/654 S; 260/652 P
[51] Int. Cl.$^2$ .................. C07C 21/08; C07C 17/38
[58] Field of Search ..................... 260/652 P, 654 S

[56] References Cited
FOREIGN PATENTS OR APPLICATIONS

1,243,169   6/1967   Germany ..................... 260/652 P

*Primary Examiner*—D. Horwitz
*Attorney, Agent, or Firm*—Spencer & Kaye

[57] ABSTRACT

A process is provided for purifying vinylidene chloride by removing dichloroacetylene. The vinylidene chloride to be purified is treated with a solution containing at least one compound selected from the group consisting of metal sulfites and metal hyposulfites to form a reaction mixture, and thereafter the purified vinylidene chloride is separated from the reaction mixture.

10 Claims, No Drawings

PROCESS FOR THE PURIFICATION OF VINYLIDENE CHLORIDE

BACKGROUND OF THE INVENTION

The present invention relates to a process for the purification of vinylidene chloride and more particularly to a process for obtaining vinylidene chloride which no longer contains significant amounts of dichloroacetylene.

Dichloroacetylene is an impurity which is frequently encountered in vinylidene chloride and which has proved to interfere greatly with the polymerization of the latter. In effect, dichloroacetylene causes chain transfer reactions during the polymerization of vinylidene chloride, resulting in a very marked reduction in the degree of polymerization.

On the other hand, a very important outlet for vinylidene chloride polymers is the manufacture of transparent films for packaging. Hence, it is essential that the starting monomer should be colorless. Now it has been found that the vinylidene chloride contaminated with dichloroacetylene discolors during storage, especially in mild steel containers, which makes the vinylidene chloride unsuitable for the manufacture of transparent polymers.

In order no longer to be objectionable, the dichloroacetylene content must not exceed about 70 ppm and preferably must be less than 50 ppm.

The presence of dichloroacetylene in vinylidene chloride is due to the process of manufacture of the latter. If vinylidene chloride is prepared by dehydrochlorination of 1,1,2-trichloroethane (or possibly 1,1,1-trichloroethane) containing small amounts of tetrachloroethanes and/or of trichloroethylene, it is found that the vinylidene chloride obtained contains dichloroacetylene arising from the dehydrochlorination of the tetrachloroethanes and/or of the trichloroethylene.

The usual techniques of purification of vinylidene chloride by distillation do not permit easy removal of the dichloroacetylene because the latter has a boiling point close to that of vinylidene chloride.

SUMMARY OF THE INVENTION

There has now been developed in accordance with the present invention, a process for reducing the content of dichloroacetylene in vinylidene chloride which in particular makes it possible to achieve dichloroacetylene contents not exceeding 70 ppm.

According to the invention, the process for reducing the dichloroacetylene content of vinylidene chloride comprises treating the vinylidene chloride to be purified with a solution containing at least one compound selected from the group consisting of metal sulfites and metal hyposulfites to form a reaction mixture and thereafter separating the purified vinylidene chloride from the reaction mixture.

DETAILED DESCRIPTION OF THE INVENTION

The metal sulfites or hyposulfites that are used in the process of the present invention react with the dichloroacetylene present in the vinylidene chloride to give products of unidentified structure which are no longer found in the vinylidene chloride after isolating the latter from the reaction mixture. Thus, vinylidene chloride which no longer contains significant quantities of dichloroacetylene is obtained.

The sulfite and/or hyposulfite can be dissolved in various solvents, but water is particularly suitable. Other solvents such as for example alcohols or mixtures of alcohols with water can also be used. Although any sulfites and hyposulfites of metals can be used, preferably the sulfites and hyposulfites of alkali metals, such as those of sodium or potassium, and the corresponding derivatives of the alkaline earth metals, such as those of magnesium and calcium, are used. Advantageously, the sulfites or hyposulfites of sodium or potassium are used. The sulfites or hyposulfites can be used individually or as a mixture.

The amount of sulfite or hyposulfite used is preferably between 0.01 and 15% by weight of the vinylidene chloride to be purified. Lower amounts only permit partial, and frequently insufficient, purification from dichloroacetylene, while higher amounts are frequently purposeless. The amount of solvent used to dissolve the sulfite or hyposulfite can vary within very wide limits. If the solvent used is water, it is advantageous to use sulfite and/or hyposulfite concentrations which lie between 0.01 g/l and the saturation concentration.

It has been found that in the process of the present invention the purification effect is the better, the more intimate is the contact achieved between the vinylidene chloride organic phase and the sulfite and/or hyposulfite solution. To ensure optimum contact, the mixture can be stirred vigorously, but it is also possible to use other known techniques, such as spraying the vinylidene chloride into the hyposulfite or sulfite solution. The purification can be carried out continuously or discontinuously.

The temperature at which the treatment is carried out can vary within very wide limits. The temperature is usually between 0° and 150° C and preferably between 50° and 120° C. Other temperatures can nevertheless also prove suitable. At the low temperatures, the rate of reaction is very slow, while at temperatures above 150° C the pressure in the reactor is particularly high, which entails the use of very costly special apparatus. The reaction pressure can be less than, equal to or greater than atmospheric pressure. As a rule, the pressure in the reactor is the autogenouspressure. This is generally between 0.5 and 20kg/cm$^2$, and most frequently between 0.8 and 10kg/cm$^2$.

The duration of the treatment can also vary within very wide limits depending on the conditions and especially on the temperature, the sulfite and/or hyposulfite concentration and the intimacy of contact between the phases in the mixture. Most frequently, the time required to effect the purification is between a few minutes and 5 hours. As will be seen from the examples described hereafter, times of between quarter of an hour and 1 hour give good results.

The purified vinylidene chloride is then separated from the mixture by any known technique such as, for example, decantation, distillation and the like.

The purification can be carried out on the vinylidene chloride which has been separated from the reaction mixture in which it has been formed. This procedure is used to purify vinylidene chloride obtained by thermal dehydrochlorination of 1,1,2- or 1,1,1-trichloroethane or by dehydrochlorination of 1,1,2-trichloroethane by means of an aqueous solution of a basic compound, in accordance with processes such as those described in the book by E. C. Leonard (Vinyl and Diene Monomer, Part 3, Wiley-Interscience, 1971, p. 1257–1259). In the latter case, the sulfite and/or hyposulfite can be directly introduced, with advantage, into the reaction mixture in which the vinylidene chloride is formed. The dichloroacetylene is thus eliminated at the rate at which it is formed. In that case, the temperature and pressure will of course be those required for the dehydrochlorination reaction to take place. Thus, the process is advantageously carried out at a temperature of 60° to 150° C and preferably under autogenous pressure. If the 1,1,2-trichloroethane is dehydrochlorinated by means of an aqueous sodium hydroxide solution, it is preferable simultaneously to introduce into the reactor an aqueous solution of sodium sulfite or sodium hyposulfite, individually or as a mixture. Of course, these latter compounds can be directly dissolved in the aqueous solution of sodium hydroxide.

The introduction of the sulfite and/or hyposulfite into the reaction mixture wherein the reaction which produces vinylidene chloride is carried out has proved to be particularly advantageous. In effect, by following this procedure, the use of a separate apparatus for carrying out the purification stage is avoided. Furthermore, it is found at the same time that the monochloroacetylene content is reduced.

If the sulfite and/or hyposulfite are introduced into the reactor wherein the alkaline dehydrochlorination of 1,1,2-trichloroethane to give vinylidene chloride is being carried out, the process can be carried out discontinuously or continuously. In the latter case, an aqueous solution of a basic compound and of a sulfite and/or hyposulfite, as well as 1,1,2-tricloroethane, are fed continuously to the reactor.

The examples which follow and which are given by way of examples only and without implying a limitation, illustrate the process which forms the subject of the present invention.

EXAMPLE 1

This example illustrates the application of the process according to the invention to the purification of vinylidene chloride which has been isolated from the reaction mixture in which it was formed.

In this example, 250 cm³ of vinylidene chloride containing only 70 ppm by weight of dichloroacetylene, and 250 cm³ of a molar aqueous solution of sodium sulfite ($Na_2SO_3$) are introduced into a 1.5 liters stainless steel autoclave.

The autoclave is closed and flushed with nitrogen, and the mixture is gradually brought to 80° C over the course of 30 minutes, with vigorous stirring (500 revolutions per minute). The reaction mixture is kept at this temperature for 40 minutes, while stirring. After this period, it is rapidly cooled to 5° C. The organic phase is separated off. The dichloroacetylene content, determined by vapor phase chromatography, is less than 5 ppm.

EXAMPLE 2

The procedure of Example 1 is repeated, except that the molar solution of sodium sulfite is replaced with a molar solution of sodium hyposulfite ($Na_2S_2O_3$).

The dichloroacetylene content after treatment is less than 5 ppm.

EXAMPLE 3

The example which follows illustrates the application of the process according to the invention to the treatment of vinylidene chloride in the reactor in which the alkaline dehydrochlorination of 1,1,2-trichloroethane is carried out.

In this example, two identical runs are made, except that in one run sodium sulfite is used, and in the second run sodium hyposulfite is used. In each run, into a 1.5 liters stainless steel autoclave, there is introduced 1 liter of a molar aqueous solution of sodium hydroxide containing 5 g/liter of either sodium sulfite ($Na_2SO_3$) or sodium hyposulfite, as well as 123.2 g of a mixture based on 1,1,2-trichloroethane and containing 7.6 g of 1,1,2,2-tetrachloroethane and 7.6 g of 1,1,1,2-tetrachloroethane.

The autoclave is closed, swept with nitrogen, placed under vacuum and then brought to 80° C in 30 minutes. The mixture is kept at this temperature for 15 minutes. The temperature is raised in an identical manner in each run. Vigorous and constant stirring is maintained throughout the duration of the run (500 revolutions per minute). At the end of the run, the mixture is cooled to 3° C. The organic phase is rapidly separated off and analyzed by vapor phase chromatography. The 1,1,2-trichloroethane is converted to vinylidene chloride with a yield of 98%, the 1,1,2,2-tetrachloroethane was converted to trichloroethylene to the extent of 100% while the 1,1,1,2-tetrachloroethane was converted to trichloroethylene to the extent of 42%.

The content of chloroacetylenic derivatives in the organic mixture obtained is summarized in Table 1 below.

By way of comparison, a comparison run is carried out in an identical manner, except that there is an absence of sodium sulfite and sodium hyposulfite. The yield of vinylidene chloride is the same in all the runs carried out.

TABLE I

| Additive | | Content of chloroacetylenic compounds, g/kg of organic phase | |
|---|---|---|---|
| Nature | Content, g/l of aqueous solution | Monochloro-acetylene | Dichloro-acetylene |
| — | — | 0.14 | 0.24 |
| $Na_2SO_3$ | 5 | 0.07 | 0.02 |
| $Na_2S_2O_3.5H_2O$ | 5 | 0.12 | 0.07 |

Examination of the results summarized under Examples 1 to 3 above shows a very marked reduction in the dichloroacetylene content on treatment of vinylidene chloride with sodium sulfite or sodium hyposulfite. If these two reagents are added to the reactor in which the vinylidene chloride is manufactured by alkaline dehydrochlorination of 1,1,2-trichloroethane, a reduction in the monochloroacetylene content is observed at the same time.

It is obvious that the process is also applicable to the purification of mixtures containing vinylidene chloride, to remove dichloroacetylene.

It will be understood that the above description of the present invention is susceptible to various modifications, changes and adaptations, and the same are intended to be comprehended within the meaning and range of equivalents of the appended claims.

What is claimed is:

1. A process for the purification of vinylidene chloride to remove dichloracetylene, comprising treating the vinylidene chloride to be purified with a solution containing at least one compound selected from the group consisting of metal sulfites of alkali metals and alkaline earth metals and metal hyposulfites of alkali metals and alkaline earth metals to form a reaction mixture and thereafter separating the purified vinylidene chloride from the reaction mixture.

2. The process according to claim 1, wherein the vinylidene chloride is treated with an aqueous solution containing said compound.

3. The process according to claim 1 wherein the compound is at least one compound selected from the group consisting of the alkali metal sulfites and alkali metal hyposulfites.

4. The process according to claim 3, wherein the compound is sodium hyposulfite.

5. The process according to claim 3, wherein the compound is sodium sulfite.

6. The process according to claim 1 wherein the amount of the compound used is between 0.01 and 15% by weight of the vinylidene chloride to be purified.

7. The process according to claim 1 wherein the temperature at which the treatment is carried out is between 0° and 150° C.

8. The process according to claim 7, wherein the temperature is between 50° and 120° C.

9. The process according to claim 2 wherein the treatment is carried out in a reactor wherein the vinylidene chloride is manufactured by dehydrochlorination of 1,1,2-trichloroethane by means of an aqueous solution of a basic compound.

10. The process according to claim 9, wherein the vinylidene chloride is treated with a solution of at least one compound selected from the group consisting of sodium hyposulfite and sodium sulfite, and said basic compound comprises sodium hydroxide.

* * * * *